US009101291B2

(12) United States Patent
Kiyan (10) Patent No.: US 9,101,291 B2
(45) Date of Patent: Aug. 11, 2015

(54) ULTRASONIC BONE ANALYSIS WITH HARMONIC AND AMPLITUDE OF THE FREQUENCIES FROM CARTILAGE TO DETERMINE THE RELATIVE RATIO OF INTEGRAL AMPLITUDE VALUES

(75) Inventor: Wataru Kiyan, Nishinomiya (JP)

(73) Assignee: Furuno Electric Company, Ltd., Nishinomiya (JP)

( * ) Notice: Subject to any disclaimer, the term of this patent is extended or adjusted under 35 U.S.C. 154(b) by 457 days.

(21) Appl. No.: 12/872,880

(22) Filed: Aug. 31, 2010

(65) Prior Publication Data

US 2011/0054313 A1 Mar. 3, 2011

(30) Foreign Application Priority Data

Sep. 1, 2009 (JP) ................ 2009-201986

(51) Int. Cl.
*A61B 8/00* (2006.01)
*A61B 8/08* (2006.01)
*A61B 5/107* (2006.01)
*A61B 5/00* (2006.01)

(52) U.S. Cl.
CPC ............ *A61B 8/0875* (2013.01); *A61B 5/1075* (2013.01); *A61B 5/4504* (2013.01); *A61B 5/4514* (2013.01); *A61B 8/0858* (2013.01)

(58) Field of Classification Search
CPC .. A61B 5/4514; A61B 8/0858; A61B 5/4504; A61B 5/1075; A61B 8/0875

USPC ........................... 600/437, 438, 443
See application file for complete search history.

(56) References Cited

U.S. PATENT DOCUMENTS

| 4,771,792 A * | 9/1988 | Seale ............... 600/587 |
| 5,564,423 A * | 10/1996 | Mele et al. ........... 600/438 |
| 2004/0193048 A1 * | 9/2004 | Tsoref ................ 600/437 |
| 2010/0030077 A1 | 2/2010 | Mori | |

FOREIGN PATENT DOCUMENTS

| JP | 2002-345821 A | 12/2002 |
| JP | 2005-125082 A | 5/2005 |
| WO | WO 03/009762 A1 | 2/2003 |
| WO | WO 2008/108054 A1 | 9/2008 |
| WO | WO2008108054 | * 12/2008 | ............... A61B 8/08 |

* cited by examiner

*Primary Examiner* — Unsu Jung
*Assistant Examiner* — Serkan Akar
(74) *Attorney, Agent, or Firm* — Alleman Hall McCoy Russell & Tuttle LLP (57) ABSTRACT

This disclosure provides an ultrasonic bone analyzing device, which includes a transmission module for transmitting an ultrasonic signal into the inside of a living body from an outer skin of the living body, a reception module for receiving an echo signal that is a reflection wave of the transmitted ultrasonic signal from the inside of the living body, and an analyzing module for generating analysis data indicative of a state of a cartilage using an amplitude value of an echo signal from the inside of the cartilage obtained from between a cartilage surface and a subchondral bone among the received echo signals.

5 Claims, 10 Drawing Sheets

ULTRASONIC BONE ANALYSIS WITH HARMONIC AND AMPLITUDE OF THE FREQUENCIES FROM CARTILAGE TO DETERMINE THE RELATIVE RATIO OF INTEGRAL AMPLITUDE VALUES

CROSS-REFERENCE TO RELATED APPLICATION(S)

The application claims priority under 35 U.S.C. §119 to Japanese Patent Application No. 2009-201986, which was filed on Sep. 1, 2009, the entire disclosure of which is hereby incorporated by reference.

TECHNICAL FIELD

The present invention relates to an ultrasonic bone analyzing device that provides quantitative information for analyzing a state of a cartilage.

BACKGROUND

Conventionally, in order to intuitively and quantitatively evaluate a state of a cartilage in an articular cavity, various types of system that apply an ultrasonic wave to the cartilage and generate analysis data based on a reflection echo.

For example, JP2002-345821(A) discloses an ultrasonic analyzing system, in which an endoscope provided with an ultrasonic transceiving body at a tip end thereof is inserted in an arthrosis, and an echo of a pulse signal which is transmitted from the ultrasonic transceiving body is acquired. Then, a wavelet transformation of the echo signal is carried out to display a cartilage thickness result which is calculated based on a cartilage surface echo level, a cartilage surface echo pulse width, and an assumed sound speed.

However, the above conventional method disclosed in JP2002-345821(A) requires a surgical operation, such as inserting the endoscope (i.e., the ultrasonic transceiving body) into a patient's body. For this reason, the patient tends to feel burdensome to have a doctor examine the cartilage state when the patient feels his/her knee being in a bad condition, which typically is an initial state of cartilage degeneration or osteoarthritis, for example.

SUMMARY

Therefore, the present invention is made in view of the situation described above, and provides an ultrasonic bone analyzing device that provides analysis data for quantitatively evaluating an accurate cartilage state, without requiring a surgical operation.

(1) According to an aspect of the invention, an ultrasonic bone analyzing device is provided, which includes a transmission module for transmitting an ultrasonic signal into the inside of a living body from an outer skin of the living body, a reception module for receiving an echo signal that is a reflection wave of the transmitted ultrasonic signal from the inside of the living body, and an analyzing module for generating analysis data indicative of a state of a cartilage using an amplitude value of an echo signal from the inside of the cartilage obtained from between a cartilage surface and a subchondral bone among the received echo signals.

(2) The analyzing module may generate the analysis data based on a value reflecting a difference in an echo level for every area of the cartilage obtained from an amplitude value of the echo signal from the inside of the cartilage and an amplitude value of the echo signal from the cartilage surface or the subchondral bone. For example, a relative ratio between an integral value of the amplitude values of the echo signals from the inside of the cartilage and an integral value of the amplitude values of the echo signals from the cartilage surface or the subchondral bone may be calculated, and the relative ratio may then be used for the analysis data.

Figure 1A:
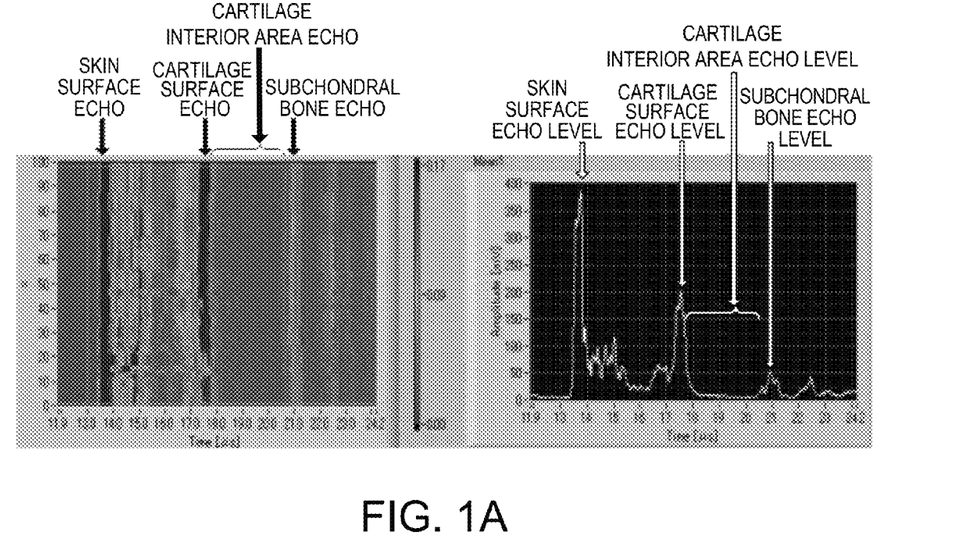
FIGS. 1A and 1B are charts showing an echo pattern in a case where it would appear that there is no cartilage degeneration, and an echo pattern in a case where it would appear that there is cartilage degeneration, respectively.
Figure 1B:
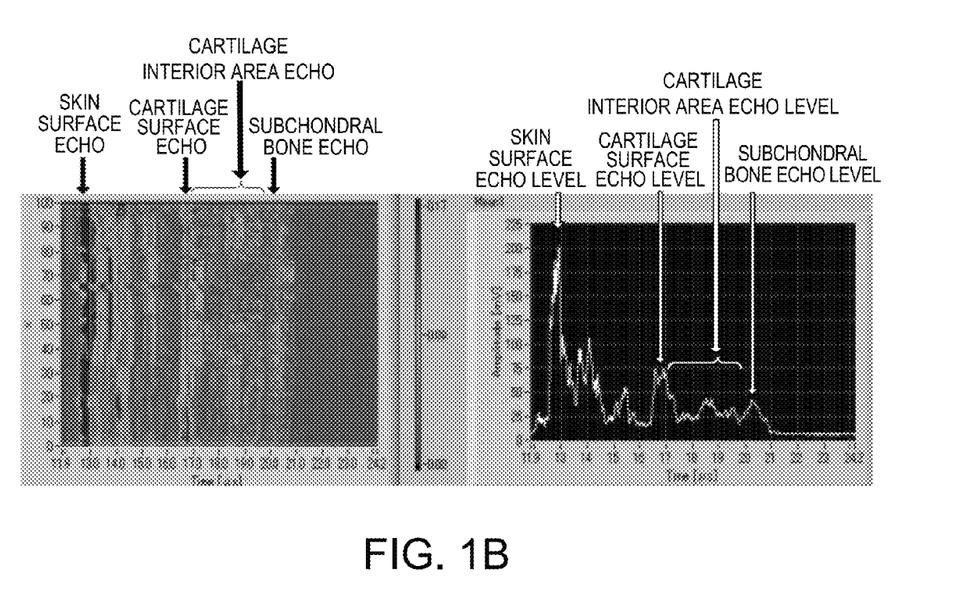

FIG. 1A shows an echo pattern in a case where it would appear that there is no cartilage degeneration, and FIG. 1B shows an echo pattern in a case where it would appear that there is cartilage degeneration. As shown in FIGS. 1A and 1B, the echo patterns differ between the case where there is no cartilage degeneration and the case where there is cartilage degeneration.

With this configuration, the cartilage is classified into two or more areas along a depth from the cartilage surface, such as a cartilage surface area, a subchondral bone area, and a cartilage interior area interposed between these areas, and the echo signal for every area is acquired as the analysis data obtained from such echo patterns. A calculated result of a relative level (amplitude value) relation of the echo signal for every area is included in the analysis data. As shown in FIG. 1A, when there is no cartilage degeneration, the echo level of the surface area is high, and the echo level of the interior area is low. On the other hand, as shown in FIG. 1B, when there is cartilage degeneration, as compared with the case where there is no cartilage degeneration, the echo level of the surface area is low, and the echo level of the interior area is high. From such a result, if the relative ratio between the echo level of the surface area and the echo level of the interior area is calculated, a difference will be caused in the relative ratio depending on the existence of cartilage degeneration.

Here, an absolute level of the echo may vary according to a state of soft tissues, such as a skin, above the cartilage surface. However, the echo from the cartilage surface and the echo from the inside of the cartilage pass through the same soft tissue area. For this reason, an influence of attenuation caused by the soft tissue can be reduced by obtaining the relative ratio between the echo level of the surface area and the echo level of the interior area. Therefore, an evaluation parameter indicative of the existence of cartilage degeneration which accurately reflects the cartilage state can be provided by including the relative relation of the echo levels for every area in the analysis data, such as the relative ratio.

(3) The transmission module may transmit an ultrasonic signal having two or more frequencies, and the analyzing module may generate the analysis data based on an amplitude value of the echo signal from the inside of the cartilage for every frequency.

With this configuration, because the ultrasonic signal can be transmitted at two or more frequencies, the analysis data can be generated for the two or more frequencies. Thereby, the analysis data of each frequency can be compared with each other, and it is easy to acquire suitable analysis data.

Figure 2A:
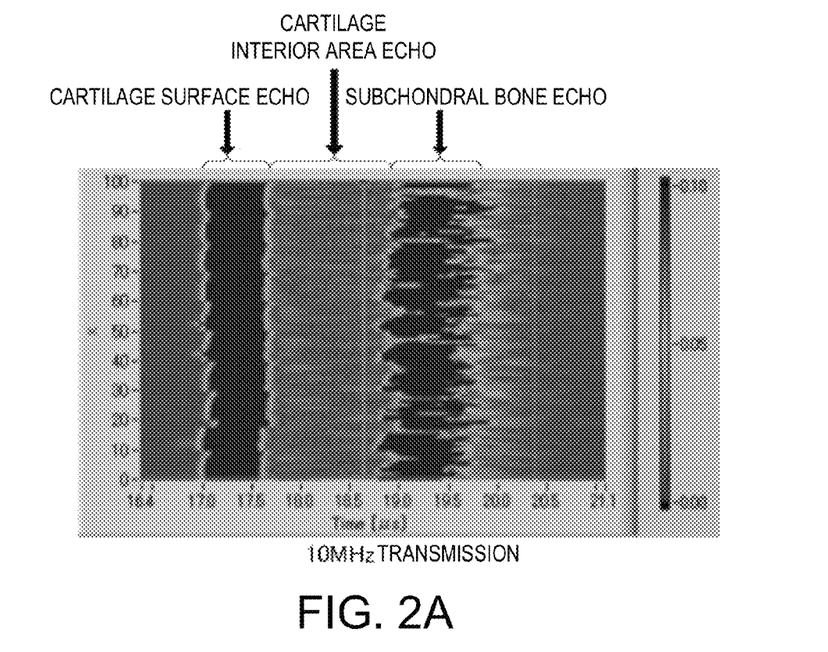
FIGS. 2A and 2B are charts showing echo patterns in a case where pulse burst signals of different frequencies are transmitted to the same sample.
Figure 2B:
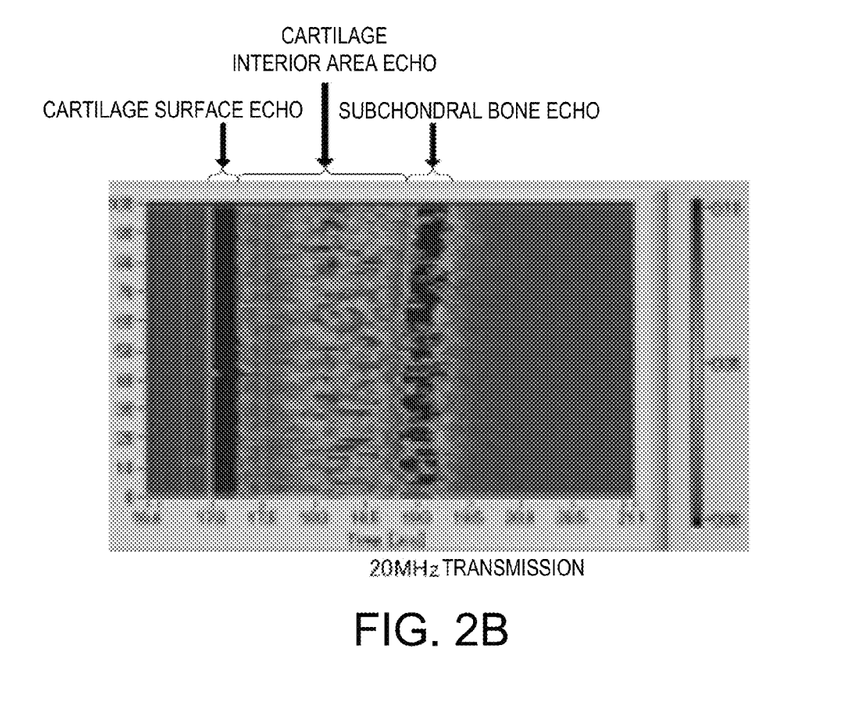

For example, FIGS. 2A and 2B show echo patterns of the ultrasonic signals at different frequencies from the same cartilage, where FIG. 2A shows a case of 10 MHz and FIG. 2B shows a case of 20 MHz. This observation result is based on an exenterate cartilage part of a pig. As shown in FIGS. 2A and 2B, the echo patterns differ if the frequency is different. For example, as shown in FIG. 2A, the echo level for the inside of the cartilage is very low at 10 MHz, and as shown in FIG. 2B, the echo level for the inside of the cartilage is higher at 20 MHz than the case of 10 MHz. Thus, because the echo levels differ according to the frequency, a frequency suitable for the echo level for forming the analysis data and a frequency not suitable for the same exist. Therefore, it is possible to generate clearer analysis data by setting the suitable frequency among two or more frequencies which can be used for the transmission.

(4) The transmission module may transmit an ultrasonic signal at a predetermined frequency, the reception module may receive an echo signal having two or more frequency components containing the predetermined frequency, and the analyzing module may generate the analysis data based on an amplitude value of the echo signal from the inside of the cartilage for every received frequency.

Figure 3:
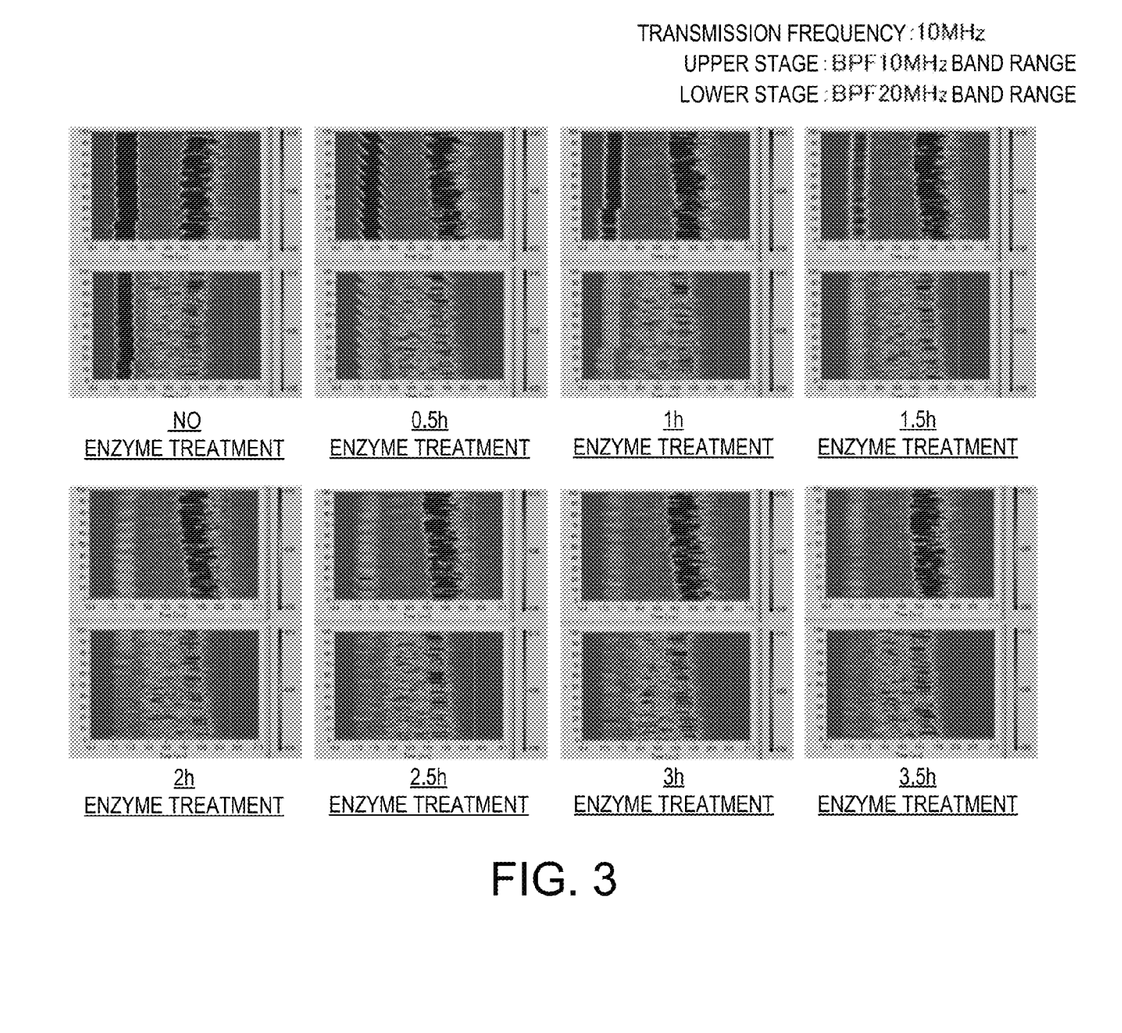
FIG. 3 are charts showing echo patterns of a fundamental frequency component and echo patterns of a secondary harmonic component, in which an echo signal caused by the pulse burst signal at a fundamental frequency (10 MHz) divided in band.

This configuration uses that a harmonic component as well as a frequency component (fundamental frequency component) of the ultrasonic signal exist in the received echo signal when the ultrasonic signal of a single frequency is transmitted. The echo data of the harmonic component appears as an echo pattern according to a harmonic frequency, not the same echo pattern as the echo data of the fundamental frequency component. For example, FIG. 3 is charts showing the echo patterns of the fundamental frequency component and the echo patterns of a secondary harmonic component in which the echo signal caused by the ultrasonic signal of the fundamental frequency (10 MHz) is divided into bands. As described above, the echo pattern of the fundamental frequency component and the echo pattern of the secondary harmonic component differ. Therefore, two or more echo patterns having different frequencies can be obtained by the single frequency ultrasonic signal.

(5) The analyzing module may detect the echo signal from the cartilage surface contained in the received echo signal based on the amplitude value of the echo signal for every frequency.

(6) The analyzing module may detect the echo signal from the subchondral bone contained in the received echo signal based on the amplitude value of the echo signal for every frequency.

Figure 4A:
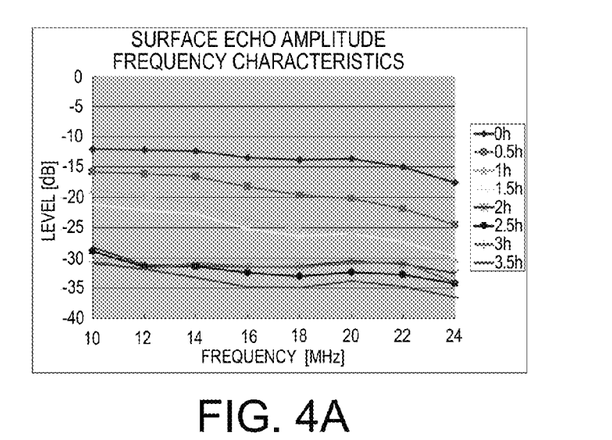
FIGS. 4A, 4B, and 4C are graphs showing a frequency characteristic of echo data from a cartilage surface, a frequency characteristic of echo data from the inside of the cartilage, and a frequency characteristic of echo data from a subchondral bone.
Figure 4B:
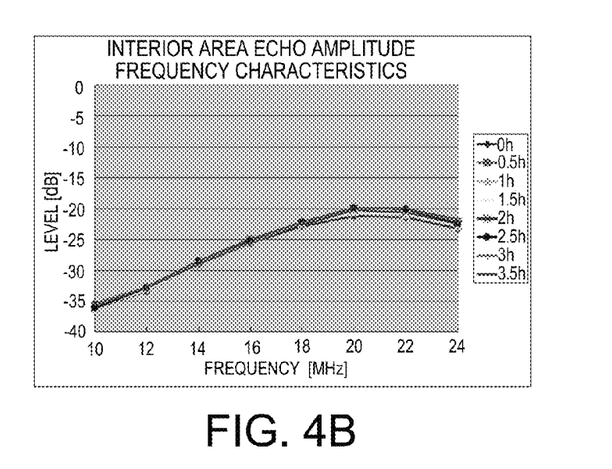
Figure 4C:
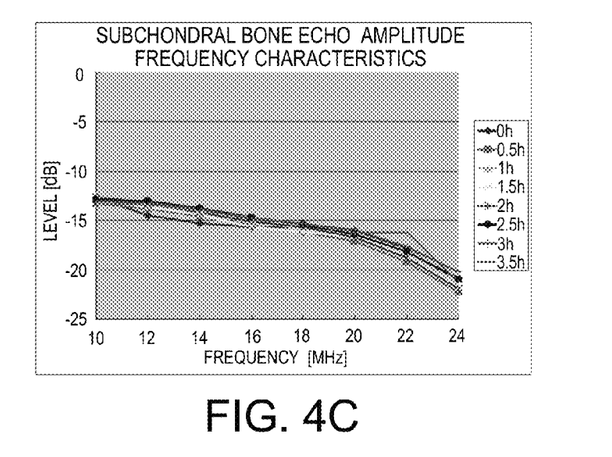

These configurations shows specific methods of determining the areas. FIGS. 4A to 4C show frequency characteristics of the echo data from each part of the cartilage, where FIG. 4A shows the frequency characteristic of the echo data from the cartilage surface area, FIG. 4B shows the frequency characteristic of the echo data from the cartilage interior area, and FIG. 4C shows the frequency characteristic of the echo data from the subchondral bone area. In FIGS. 4A to 4C, two or more characteristic curves shown in each of the characteristic chart show characteristics of a case where there is no cartilage degeneration and a case where the cartilage degeneration is empirically advanced, respectively. As shown in FIGS. 4A to 4C, because the frequency characteristics differ for each part of the cartilage (the cartilage surface, the subchondral bone, and the inside of the cartilage located therebetween), the areas can be classified based on the frequency characteristics.

(7) The transmission module may transmit a chirp-like ultrasonic signal as the ultrasonic signal.

This configuration shows a transmission control for acquiring the echo signals of two or more frequencies, and can implement two or more frequencies within a single ultrasonic signal by using the chirp-like ultrasonic signal.

(8) The transmission module may transmit the ultrasonic signals of different frequencies at different timings.

This configuration also shows the transmission control for acquiring the echo signals of two or more frequencies, and can sequentially acquire, by sequentially transmitting the ultrasonic signals of different frequencies, the echo signals of different frequencies for every transmitted ultrasonic signal.

The transmission module may transmits a plurality of ultrasonic signals. The analyzing module may evaluate angles of incident of the plurality of ultrasonic signals to the cartilage surface based on reception times of echoes from the cartilage surface produced by the plurality of ultrasonic signals, and generate the analysis data based on the amplitude value of the echo signal which the angle of incident is substantially 90 degrees.

As described above, according to the aspect of the present invention, the analysis data of cartilage degeneration, which is quantitative and intuitive, can be provided without performing a surgical operation, where the analysis data is not influenced by the state of soft tissues, such as a skin.

BRIEF DESCRIPTION OF THE DRAWINGS

The present disclosure is illustrated by way of example and not by way of limitation in the figures of the accompanying drawings, in which the like reference numerals indicate like elements and in which.

DETAILED DESCRIPTION

Several embodiments of an ultrasonic bone analyzing device according to the invention are described with reference to the appended drawings.

First Embodiment

Figure 5A:
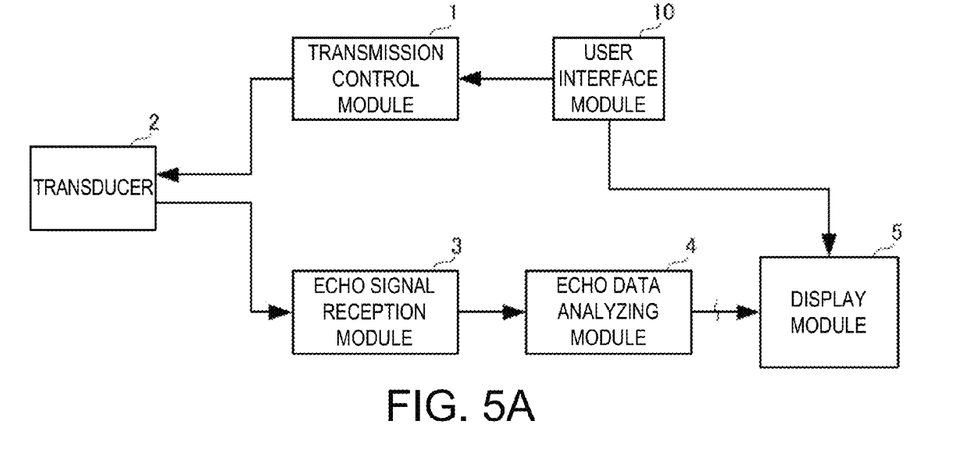
FIGS. 5A and 5B are block diagrams showing a substantial configuration of an ultrasonic bone analyzing device according to a first embodiment of the invention.
Figure 5B:
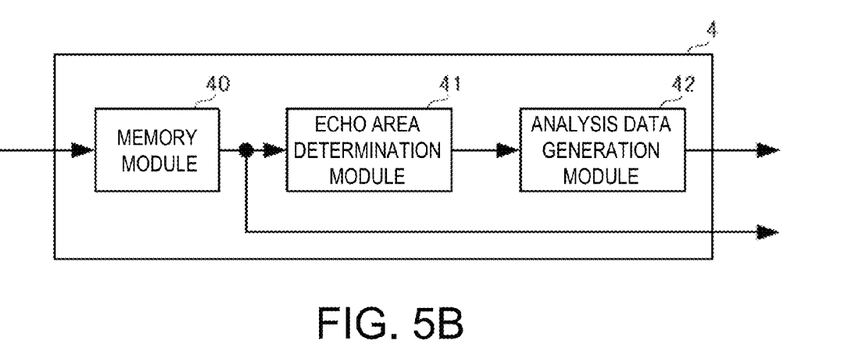

FIGS. 5A and 5B are block diagrams showing a substantial configuration of an ultrasonic bone analyzing device according to a first embodiment of the invention. Below, the embodiment is described for a cartilage of a person's knee as an example of a detection object. Note that the configuration of this embodiment may also be applied to other devices which analyze an internal structure of the detection object from the outside of the detection object by using an ultrasonic signal, similar to the ultrasonic bone analyzing device.

As shown in FIGS. 5A and 5B, the ultrasonic bone analyzing device of this embodiment includes a transmission control module 1, a transducer 2, an echo signal reception module 3, an echo data analyzing module 4, a display module 5, and a user interface module 10.

A user operates the user interface module 10 to input information on transmission to set transmission parameters, such as a transmission frequency, a pulse width, an input voltage, and the user interface module 10 then gives the inputted transmission parameters to the transmission control module 1. The user interface module 10 also gives a setting or an instruction to change a display mode of the display module 5 according to a user's input of display information. Alternatively, the user interface module 10 may be incorporated into the display module 5.

The transmission control module 1 generates a drive signal for transmitting a pulse burst signal to the transducer 2 according to the user's input from the user interface module 10 or a frequency and a transmission timing interval which are set in advance. Note that, although an example where the pulse "burst" signal which pulse length is relatively long is used as the ultrasonic signal is shown in the following description, a pulse signal which pulse length is relatively short may also be used according to specifications of the device or situations where the device is used.

The transmission control module 1 and the transducer 2 have a configuration in which they can transmit the pulse burst signal at two or more transmission frequencies. For example, they may be configured to transmit the pulse burst signal at specific frequencies within a predetermined frequency band, such as about 10 MHz to 24 MHz. Here, the pulse burst signal is a signal that forms a pulse waveform by continuously transmitting a carrier wave, which is set at the above-described frequency, over a predetermined cycle. The pulse waveform part serves as a transmitting section, and the sections other than the pulse waveform part serve as a receiving section. The receiving section is set longer than a period from a timing at which the pulse burst signal is transmitted to the person's knee to a timing at which the transducer 2 receives the reflection signal of the pulse burst signal which reached a depth (distance) set in advance.

The frequency of the pulse burst signal is set in advance to a frequency suitable for acquiring echo data suitable for evaluating the person's cartilage and analysis data for the cartilage by using empirical results, or set to two or more frequencies adjusted by the user through the user interface module 10 after acquiring the analysis data such as the echo patterns by the pulse burst signal at two or more frequencies as described later.

The transducer 2 is encased in a casing having a form suitable for being used by an operator while being contacted to an outer skin of the knee (for example, a casing similar to one for a hand-held scanner). The transducer 2 transmits the pulse burst signal with a predetermined directivity by a drive signal given from the transmission control module 1. The transducer 2 receives a reflection signal containing echoes reflected from respective parts of the knee including a cartilage surface, an inside of the cartilage, and a subchondral bone, then converts the echoes into electric signals, and outputs them to the echo signal reception module 3.

The echo signal reception module 3 carries out filter processing of the echo signals with a bandpass filter BPF which has a pass band of a frequency band of the pulse burst signal. For example, if the transmission frequency of the pulse burst signal is 10 MHz, the echo signal reception module 3 carries out the filter processing with the BPF of, for example, 40% of a fractional band width, with the center frequency being 10 MHz. The echo signal reception module 3 samples the filter-processed echo signals at predetermined sampling timings to form the entire echo data where the partial echo data sampled in the depth direction from the surface of the knee are arranged. That is, the entire echo data (hereinafter, simply referred to as "echo data") for 1PING having a group of partial echo data where the partial echo data are arranged at given intervals in the depth direction. The echo signal reception module 3 outputs the echo data corresponding to the pulse burst signal for one time to the echo data analyzing module 4 as the echo data for 1PING.

The echo data analyzing module 4 generates the analysis data for the cartilage by using the inputted echo data, and then outputs the echo data for a predetermined number of PINGs to the display module 5 along with the analysis data for the cartilage.

Hereinafter, a method of generating the analysis data, which is implemented by the echo data analyzing module 4, is specifically described. As shown in FIG. 5B, the echo data analyzing module 4 includes a memory module 40, an echo area determination module 41, and an analysis data generation module 42.

The memory module 40 has a storage capacity of the echo data for the predetermined number of PINGs, and sequentially stores the echo data for every single PING inputted from the echo signal reception module 3. Here, when new echo data is inputted in a case where echo data are stored to the limit of the storage capacity, processing for rewriting the echo data of the oldest PING with the new echo data is performed. Thereby, the echo data for the predetermined number of newest PINGs are stored in the memory module 40.

The echo area determination module 41 acquires the echo data from the memory module 40, and then determines an echo area. For the determination of the echo area, a soft tissue area (such as the skin including the outer skin area), a cartilage surface area, a cartilage interior area, and a subchondral bone area may be set corresponding to the partial echo data which are arranged in the depth direction (i.e., a time-series arrangement) based on a lapsed time from a transmission timing. Note that a relation between the lapsed time and each area may be empirically acquired in advance. However, because a thickness (depth) of each area varies with person, it may be better to use one or both of the following methods. Note that, as one of features of the device of this embodiment, the device is able to distinguish the cartilage surface area, the cartilage interior area, and the subchondral bone area, or the device is able to distinguish at least the cartilage surface area and the cartilage interior area.

(i) Determination by Temporal (Depth Direction) Change in Level of Echo Data

If the pulse burst signal set to the frequency suitable for observation is used, the echo data will have a specific echo pattern regardless of the existence of the cartilage degeneration, as shown in FIGS. 1A and 1B. Specifically, if the soft tissue area (such as the skin including the outer skin area), the cartilage surface area, the cartilage interior area, and the subchondral bone area are set in the depth direction in this order as absolute levels, the cartilage interior area normally has the absolute level lower than those of the cartilage surface area and the subchondral bone area which are adjacent to the cartilage interior area.

By using the characteristic of the echo level in the depth direction, for example, when the echo level increases rapidly in the depth direction above a first level difference threshold, a depth position not substantially at "0" (substantially "0" in the time-axis) is set to an end of the cartilage surface area on the skin surface side (a boundary with the soft tissue area, such as the skin). Then, as the depth is taken deeper, a point where the echo level decreases rapidly below a second level difference threshold is set to a border between the cartilage surface area and the cartilage interior area. As the depth is further taken deeper, a point where the echo level increases rapidly over a third level difference threshold is set to a border between the cartilage interior area and the subchondral bone area. Note that the third level difference threshold for determining the boundary between the cartilage interior area and the subchondral bone area is set lower than the first level difference threshold for determining the cartilage surface area.

By using such a change in the echo level in the depth direction, the cartilage surface area, the cartilage interior area, and the subchondral bone area can be classified.

(ii) Determination by Frequency Characteristic of Echo Data

The above-described method (i) is effective if there is no cartilage degeneration or if it is in an early stage of degeneration. However, if the cartilage degeneration advances, the echo level of the cartilage surface area will decrease and the echo level of the cartilage interior area will increase. Thereby, the boundary may not be clearly distinguished. For this reason, the area classification is performed in this embodiment by using the frequency characteristic for every area as shown in FIGS. 4A to 4C.

As shown in FIGS. 4A to 4C, the echo level has a different frequency characteristic in each part of the cartilage (i.e., the cartilage surface area, the cartilage interior area, and the subchondral bone area). For example, as shown in FIG. 4A, in the cartilage surface area, the echo level decreases with an increase of the transmission frequency in the predetermined frequency range (10 MHz to 24 MHz). As shown in FIG. 4B, in the cartilage interior area, the echo level increases in the predetermined frequency range (10 MHz to 24 MHz) with the increase in the transmission frequency. The echo data then decreases after it reaches a local maximum value (about 21 MHz). As shown in FIG. 4C, in the subchondral bone area, the echo level decreases with the increase of the transmission frequency in the predetermined frequency range (10 MHz to 24 MHz). Here, the cartilage surface area and the subchondral bone area similarly have characteristics in which the echo level decreases with the increase of the transmission frequency. However, because the cartilage interior area exists between the cartilage surface area and the subchondral bone area, the echo data arranged in the depth direction do not overlap with each other.

Such frequency characteristics are used, first, each pulse burst signal is transmitted at different transmission frequencies for every PING, and respective echo data are acquired. Then, the plural partial echo data of the plurality of PINGs (at two or more frequencies) for each depth position are read out to acquire the frequency characteristics. Although, in this embodiment, the example in which the pulse burst signals with different transmission frequencies are sequentially transmitted, the pulse burst signal may be a chirp-like pulse burst signal where the frequency of the carrier wave changes within one pulse. If the chirp-like pulse burst signal is used, the echo data of the plurality of frequencies can be acquired only by one transmission, for example.

Then, based on the frequency characteristics of the partial echo data for every depth position, it is determined which area the partial echo data of each depth position belongs, respectively (i.e., the cartilage surface area, the cartilage interior area, and the subchondral bone area). Then, the depth position and each area are made associated with each other, and, further, the lapsed time from the transmission timing in each transmission frequency and each area are made associated with each other.

After the area classification by such frequency characteristics is completed, the pulse burst signal of the specific single frequency set in advance is transmitted sequentially, and echo data is acquired sequentially. Here, because a classification criterion of each area is stored in a form of the lapsed time for every transmission frequency, it can be determined which area the partial echo data which constitutes the echo data belongs based on the lapsed time.

As described above, after the area classification of the echo data is carried out, the echo area determination module 41 outputs the determined echo data to the analysis data generation module 42.

When the echo data is acquired from the echo area determination module 41, the analysis data generation module 42 extracts the classified-by-area echo data of at least the cartilage surface area and the cartilage interior area, and calculates relative ratio data as the analysis data for the cartilage.

More specifically, if the relative ratio data is calculated for every PING a maximum value of the echo level is calculated based on the partial echo data at two or more depth positions included in the classified-by-area echo data of the cartilage surface area in 1PING, for example. In addition, the maximum value of the echo level is calculated based on the partial echo data at two or more depth positions included in the classified-by-area echo data of the cartilage interior area in 1PING. Then, the relative ratio data for every PING is calculated by calculating a ratio of the maximum value of the echo level of the cartilage surface area and the maximum value of the echo level of the cartilage interior area.

When using echo data of two or more PINGs, the maximum value of the echo level is calculated based on the partial echo data group which constitutes the classified-by-area echo data of the cartilage surface area for a predetermined number of PINGs. In addition, the maximum value of the echo level is calculated based on the partial echo data group which constitutes the classified-by-area echo data of the cartilage interior area for the predetermined number of PINGs. In addition, a relative ratio data using the echo data for two or more PINGs is calculated by calculating a ratio of the maximum value of the echo data of the cartilage surface area and the maximum value of the echo level of the cartilage interior area. Alternatively, as another method, the echo data of two or more PINGs may be synchronized and added at a suitable reference, and the maximum value for each area is then calculated. Then, the relative ratio data may be calculated by calculating the ratio of the maximum value for each area.

Although, in the above description, the case where the maximum value of the echo level is used is disclosed, an integral value of the echo levels of the partial echo data may be calculated for every area, and the relative ratio data may be calculated based on the integral value. Alternatively, instead of the integral value, the relative ratio may be calculated using a value reflecting the echo level for each area (a median value, a mean value or the like of the two or more echo levels).

By using the relative ratio of the echo level of the cartilage surface area and the echo level of the cartilage interior area, quantitative data only according to the existence and the state of the cartilage degeneration can be calculated, without being influenced by the state of the soft tissues, such as the skin. This is based on the following reasons.

(1) Both the echo from the cartilage surface area and the echo from the cartilage interior area utilize the echoes passing through the soft tissue area, such as the skin. In addition, by dividing the echo levels mutually, the influence of the soft tissue area, such as the skin, can be reduced.

(2) As shown in FIGS. 1A and 1B, if there is no cartilage degeneration, the echo level of the cartilage interior area is very low with respect to the echo level of the cartilage surface area, and if there is no cartilage degeneration, the echo level of the cartilage interior area is higher than the case where there is cartilage degeneration, with respect to the echo level of the cartilage surface area. Therefore, if the denominator of the relative ratio is set to the echo level of the cartilage surface area and the numerator is set to the echo level of the cartilage interior area, the relative ratio will be significantly high when there is cartilage degeneration, as compared with the case where there is no cartilage degeneration.

The echo data analyzing module 4 outputs the relative ratio data calculated in this way and the echo data stored in the memory module 40 to the display module 5 as the analysis data.

Figure 6:
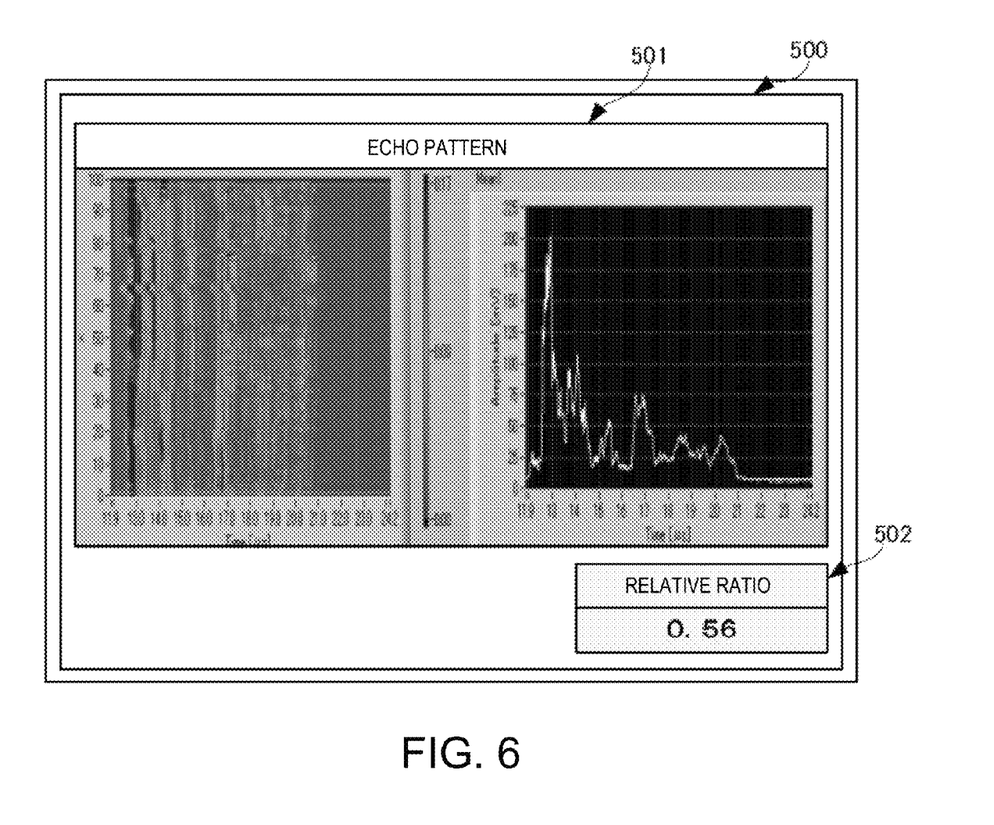
FIG. 6 is a diagram showing a form of a display image of the first embodiment.

The display module 5 displays an echo pattern image based on the echo data and a text image of the relative ratio in a display screen. FIG. 6 is a diagram showing a form of the display image of this embodiment. As shown in FIG. 6, on the display screen image 500, an echo pattern display window 501 and a relative ratio display window 502 are displayed. In the echo pattern display window 501, an echo pattern image which covers two or more PINGs and displays the echo data two-dimensionally is included, where the horizontal axis is set to a depth (time) and the vertical axis is set to a PING number. The echo pattern display window 501 also includes an echo level image, where the horizontal axis is set to the depth (time) and the vertical axis is set to the echo level. Here, the echo pattern image is displayed so as to be classified by color according to the levels of the partial echo data. Thereby, the user can visually recognize the echo level from each part of the cartilage intuitively.

In the echo level image, an envelope curve is displayed, wherein the average value and the maximum value of the partial echo data of two or more PINGs are calculated at each depth position (position on the time-axis), and the curve envelops the average values and the maximum values sequentially in the depth direction. Thereby, the user can visually recognize the echo level from each part of the cartilage intuitively and quantitatively.

In relative ratio display window 502, a numerical value of the calculated relative ratio is displayed. Thereby, the user can visually recognize intuitively, quantitatively and clearly the relative ratio of the echo level of the cartilage surface area and the echo level of the cartilage interior area.

As described above, by using the configuration of this embodiment, the information for evaluating the existence of cartilage degeneration can be provided to the user intuitively, quantitatively and clearly.

In the display screen image 500 of this embodiment, the display color of the relative ratio display window 502 may be changed according to the value of the relative ratio data. Thereby, the indication which is further excellent in the visibility according to a cartilage-like object can be performed.

Second Embodiment

Next, an ultrasonic bone analyzing device according to a second embodiment is described with reference to the appended drawings. In the ultrasonic bone analyzing device of the first embodiment described above, the pulse burst signal at single frequency is used and only the frequency band component of the pulse burst signal in the echo signal is used. However, in the ultrasonic bone analyzing device of this embodiment, a frequency band component (fundamental frequency band component) of the pulse burst signal in the echo signal and a harmonic component (second harmonic component) are used.

Figure 7:
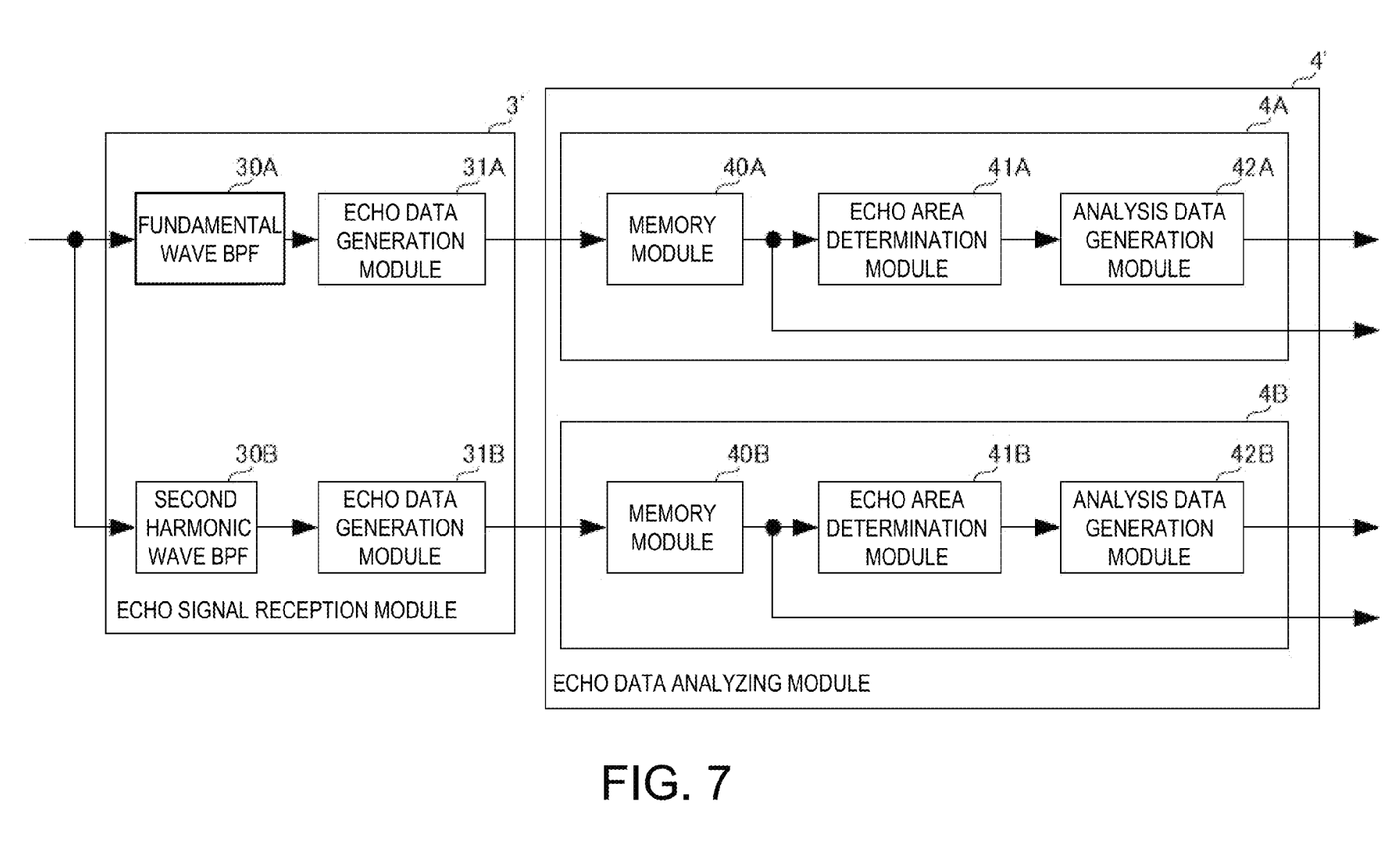
FIG. 7 is a block diagram showing a configuration of an echo signal reception module 3' and an echo data analyzing module 4' of an ultrasonic bone analyzing device according to a second embodiment of the invention.

FIG. 7 is a diagram showing a configuration of an echo signal reception module 3' and an echo data analyzing module 4' of the ultrasonic bone analyzing device of this embodiment.

As shown in FIG. 7, in the echo signal reception module 3' of this embodiment, an echo signal is inputted into a fundamental wave bandpass filter (BPF) 30A and a second harmonic wave bandpass filter (BPF) 30B. The fundamental wave BPF 30A is a bandpass filter having a predetermined frequency band as its pass band, where the fundamental wave component (transmission frequency component of the pulse burst signal) in the echo signal is its center frequency. Thereby, the fundamental wave BPF 30A outputs the fundamental frequency component of the echo signal to the echo data generation module 31A. The echo data generation module 31A samples the fundamental frequency component of the echo signal at a sampling interval according to the fundamental frequency to generate echo data where partial echo data are arranged in a time series (i.e., in the depth direction). The echo data of the generated fundamental frequency component is outputted to a fundamental frequency component analyzing module 4A of the echo data analyzing module 4'.

The second harmonic wave BPF 30B is a bandpass filter having a predetermined frequency band width as its pass band, where the second harmonic wave component (second harmonic frequency with respect to the transmission frequency of the pulse burst signal) in the echo signal as its center frequency. Thereby, the second harmonic wave BPF 30B outputs the second harmonic wave frequency component of the echo signal to the echo data generation module 31B. The echo data generation module 31B samples the second harmonic wave frequency component of the echo signal at a sampling interval according to the second harmonic wave frequency to generate echo data where partial echo data are arranged in a time series (i.e., in the depth direction). The echo data of the generated second harmonic wave frequency component is outputted to a second harmonic wave frequency component analyzing module 4B of the echo data analyzing module 4'.

The fundamental frequency component analyzing module 4A includes a memory module 40A, an echo area determination module 41A, an analysis data generation module 42A, which is a similar configuration to the echo data analyzing module 4 of the first embodiment described above. The analysis data generation module 42A calculates the relative ratio data based on the fundamental wave, and outputs it along with the echo data of the fundamental wave stored in the memory module 40A, collectively as fundamental wave analysis data.

The second harmonic wave frequency component analyzing module 4B includes the memory module 40A, the echo area determination module 41B, the analysis data generation module 42A, which is a similar configuration to the echo data analyzing module 4 of the first embodiment or the fundamental frequency component analyzing module 4A described above. The analysis data generation module 42B calculates the relative ratio data based on the second harmonic wave, and outputs it along with the echo data of the second harmonic wave stored in the memory module 40B, collectively as second harmonic wave analysis data.

Figure 8:
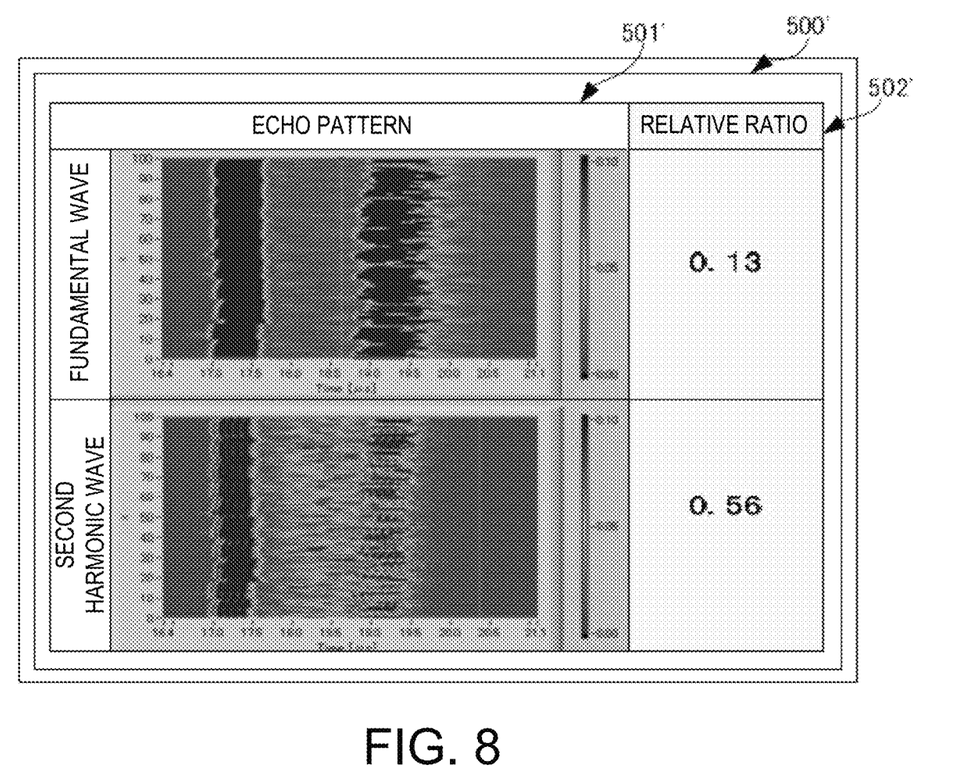
FIG. 8 is a diagram showing a form of a display image of the second embodiment.

The display module 5 displays an echo pattern image based on the fundamental wave echo data and the second harmonic wave echo data on a display screen using the fundamental wave analysis data and the second harmonic wave analysis data, and displays the relative ratio of the respective frequencies. FIG. 8 is a diagram showing a form of a display image of this embodiment. As shown in FIG. 8, a display screen image 500' has an echo pattern display window 501' and a relative ratio display window 502' which are displayed side-by-side. The echo pattern and the relative ratio data of the fundamental wave are displayed on the upper half of each window, and the echo pattern and the relative ratio data of the second harmonic wave are displayed on the lower half.

Because such a display form is used, the analysis data according to two or more frequencies can be displayed intuitively, quantitatively and clearly. Thereby, more determination information for the existence of cartilage degeneration can be displayed. In addition, because such an echo pattern of two or more frequencies is displayed, information for determining whether the frequency setting is suitable can also be provided. For example, in the case of FIG. 8, at the fundamental frequency, the echo of the cartilage interior area is too low, and the reliability of the relative ratio may become low. However, at the second harmonic wave frequency, the echo level of the cartilage interior area can be obtained at a predetermined level and, thus, it can check that the reliability of the relative ratio is higher than the relative ratio of the fundamental frequency. Using this, the user can refer to the more probable relative ratio of the echo pattern, and can use it to adjust the transmission frequency.

Further, in this embodiment, the generation of the analysis data based on such a second harmonic frequency can be performed based on the pulse burst signal at the single frequency. Therefore, the analysis data containing more information can be generated and displayed without transmitting the pulse burst signal at two or more frequencies.

The image of the echo level pattern as shown in the first embodiment may also be displayed on the display screen image 500' of this embodiment for every frequency. Thereby, even more and usable information can be displayed.

In this embodiment, the echo data of the fundamental frequency and the echo data of the second harmonic wave frequency are acquired based on the pulse burst signal of the single frequency (fundamental frequency), and the analysis data is generated based on the pattern where echo levels are arranged on the time-axis (in the distance (depth) direction) for every frequency. However, a level ratio of the echo data of respective frequencies corresponding to the same distance position may be calculated, and it may be used for the analysis data.

Note that, although the above description of this embodiment does not describe in detail, as for the method of classifying the echo data into the cartilage surface area, the cartilage interior area, and the subchondral bone area, a similar method to the first embodiment may be used. In this embodiment, the above classification may also be performed using either one of the fundamental wave echo data and the second harmonic wave echo data.

Third Embodiment

Next, an ultrasonic bone analyzing device according to a third embodiment is described with reference to the appended drawings. In the first and second embodiments, the analysis data is generated using the pulse burst signal at the single frequency. However, in the ultrasonic bone analyzing device of this embodiment, more information to be contained in the analysis data is added using the pulse burst signal at two or more frequencies. The ultrasonic bone analyzing device of this embodiment has a similar fundamental block configuration to the ultrasonic bone analyzing device of the first or second embodiment. Below, an example in which the pulse burst signal of two or more frequencies is transmitted in the ultrasonic bone analyzing device of the first embodiment is illustrated.

The transmission control module 1 drives the transducer 2 so that the pulse burst signals of two or more of frequencies at predetermined frequency intervals within the user's input from the user interface module 10 or the predetermined frequency band are transmitted sequentially. Here, after the transmission on each setting frequency of the set entire frequency band is completed, the transmissions of the pulse burst signals are similarly repeated again, while sequentially changing frequency.

The transducer 2 transmits the pulse burst signal at each frequency, receives the echo signal, and then outputs it to the echo signal reception module 3. The echo signal reception module 3 carries out filter processing of each echo signal with the bandpass filter to which the pass band is set with the transmission frequency of the pulse burst signal which corresponds for every echo signal as described above. Then, the echo signal reception module 3 samples the echo signal, which is filter-processed by each frequency band, according to the frequency to generate echo data where partial echo data are arranged in the depth direction.

The echo data analyzing module 4 acquires the echo data at each frequency, and as described above, using the time changes (depth changes) and the frequency characteristics, it performs the area classification so that at least the cartilage surface area and the cartilage interior area are classified. Then, the echo data analyzing module 4 calculates the relative ratio data by calculating the relative ratio between the maximum value of the echo data of the cartilage surface area and the maximum value of the echo data of the cartilage interior area.

Figure 9:
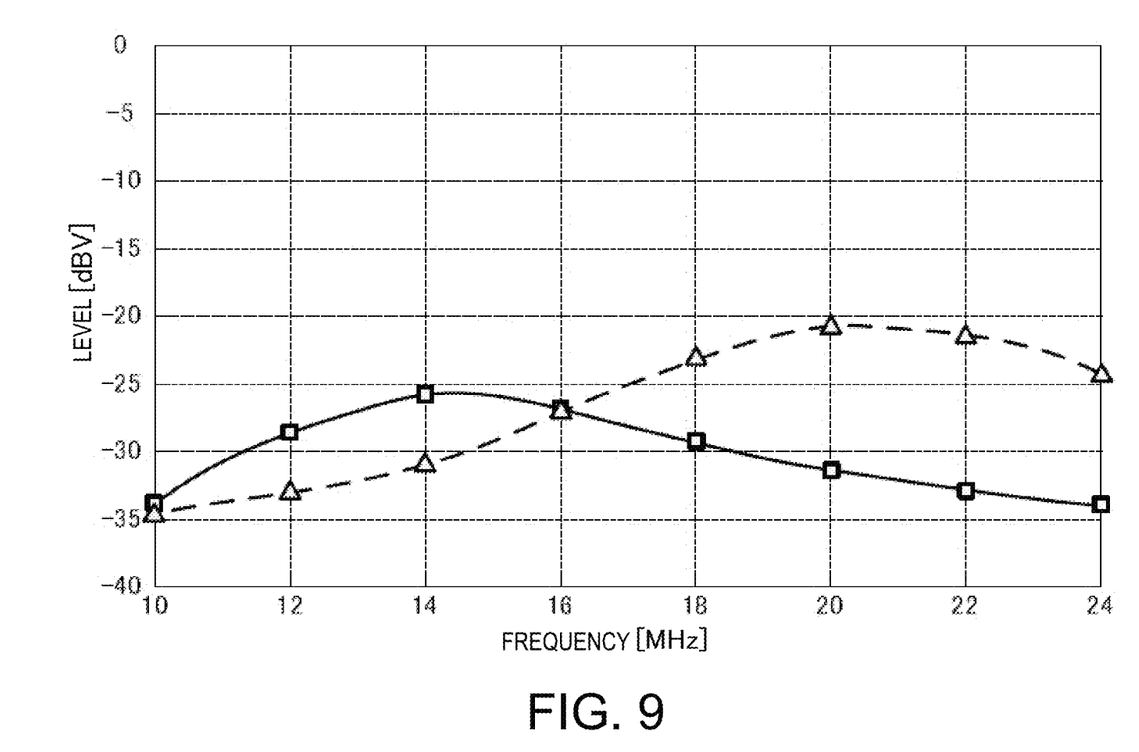
FIG. 9 is a diagram showing a frequency characteristic of an echo level for the inside of the cartilage.

The echo data analyzing module 4 of this embodiment calculates the frequency characteristics of the echo data of the cartilage interior area as shown in FIG. 9 based on the echo data at each frequency corresponding to the cartilage interior area. FIG. 9 is a diagram showing the frequency characteristic of the echo level for the inside of the cartilage. More specifically, for example, the partial echo data group in each echo data, which is classified into the cartilage interior area as described above, is further classified into frequencies. Then, the maximum and the average value of the partial echo data group at each frequency are calculated, and the frequency characteristic is acquired by associating them with the frequency.

The echo data analyzing module 4 outputs the stored echo data, the relative ratio data, and the frequency characteristic to the display module 5 as analysis data.

Figure 10:
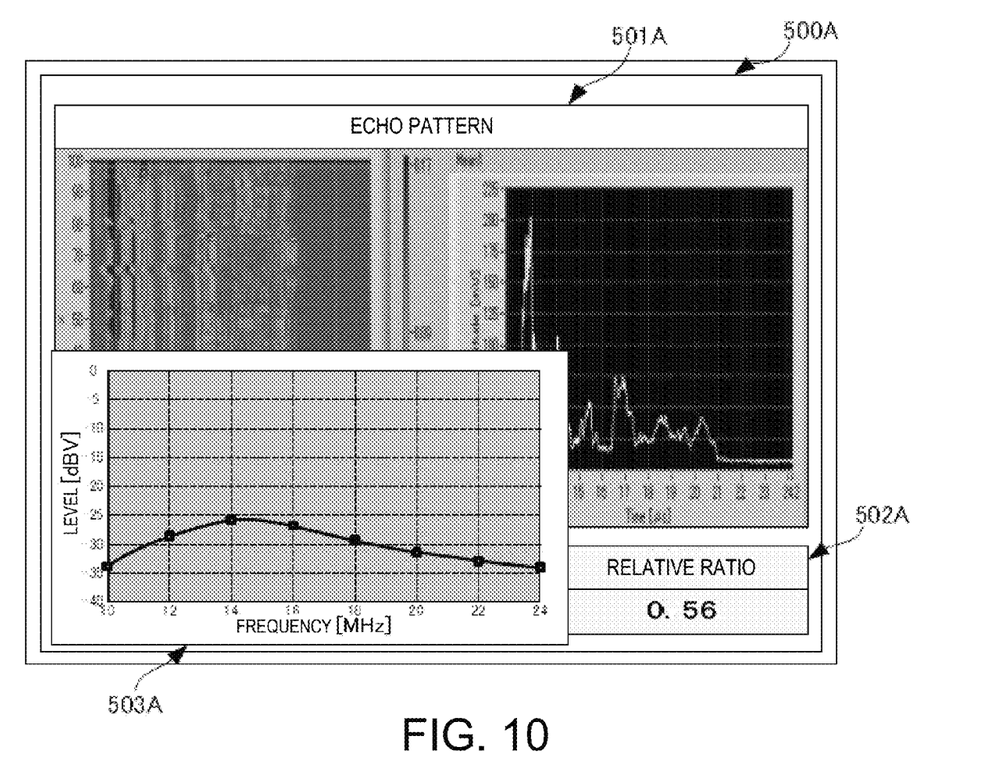
FIG. 10 is a diagram showing a form of a display image according to a third embodiment of the invention.

The display module 5 displays an echo pattern image based on the echo data and a text image of the relative ratio on a display screen. FIG. 10 is a diagram showing a form of the display image of this embodiment. As shown in FIG. 10, in the display screen image 500A, an echo pattern display window 501A, a relative ratio display window 502A, and a frequency characteristic display window 503A are displayed. In the echo pattern display window 501A, the echo pattern and the echo level image are displayed similar to the first embodiment. In the relative ratio display window 502, a numerical value of the calculated relative ratio data is displayed. In the frequency characteristic display window 503A, the calculated frequency characteristic is displayed. Although, in FIG. 10, the frequency characteristic display window 503A is displayed so as to overlap with the echo pattern display window 501A or the relative ratio display window 502A, they may also be displayed so as not to overlap with each other if the display module is large enough. If in the case where the windows overlap with each other, a user may perform a selection operation by using a pointing device or the like to display a selected window on the forefront side, or change a size of the window.

As described above, by using the configuration of this embodiment, the analysis data also including the frequency characteristic which changes with the state of the cartilage interior area can be further displayed, and more information for evaluating the state of the cartilage can be displayed.

In the above description, the measurement is made without moving the tip of the transducer while the transducer contacts the skin. However, while the tip of the casing containing the transducer contacting the skin, a user may rotate the rear end to change the transmitting direction of the pulse burst signal to acquire the echo signals over a predetermined area. Alternatively, the echo signals may also be acquired while moving the casing itself containing the transducer. In these cases, the echo area determination module 41, with reference to the detected outer skin side end part of the cartilage surface area, may perform an alignment in the depth direction of the partial echo data which constitutes the echo data. Thereby, the influence of the depth difference for the partial echo data for every echo data due to the difference in the transmitting direction of the pulse burst signal can be eliminated, and more accurate analysis data can be generated.

Further, in the above description, the number of transducers is one. However, two or more transducers may be arrayed in the casing, beam forming may be carried out, and electronic scanning or the like may be used, to generate the analysis data for a predetermined area. Alternatively, two or more transducers may be arrayed in the casing, and a data selection module may be provided. The data selection module may evaluate angles of incident of the pulse burst signals to the cartilage surface based on incoming times of echoes from the cartilage surface which the respective transducers receive, and obtain the analysis data based on the echo signals which the angles of incident is substantially 90 degrees.

In the above description, the casing of the transducer contacts the skin. However, if an ultrasonic transducer having a narrow focal area in the depth direction is used, the transducer may be separated from the skin so that the transducer focuses on the cartilage. In this case, similar to the case where the casing is rotated and moved, the alignment in the depth direction of the partial echo data which constitutes the echo data, with respect to the outer skin side end part of the cartilage surface area.

In the above description, the memory modules 40, 40A, and 40B are provided in the echo data analyzing module 4 and 4'. However, they may be provided in front of the echo signal reception module 3, for example.

In the above description, the relative ratio of the echo levels for each area is calculated and it is used for the analysis data. However, a difference value of the echo levels for each area may be calculated, and it may be used for the analysis data. Alternatively, it may be other calculated values reflecting a difference of the echo data for each area.

In the foregoing specification, specific embodiments of the present invention have been described. However, one of ordinary skill in the technique appreciates that various modifications and changes can be made without departing from the scope of the present invention as set forth in the claims below. Accordingly, the specification and figures are to be regarded in an illustrative rather than a restrictive sense, and all such modifications are intended to be included within the scope of the present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

Moreover in this document, relational terms such as first and second, top and bottom, and the like may be used solely to distinguish one entity or action from another entity or action without necessarily requiring or implying any actual such relationship or order between such entities or actions. The terms "comprises," "comprising," "has," "having," "includes," "including," "contains," "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a," "has . . . a," "includes . . . a," "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially," "essentially," "approximately," "about" or any other version thereof, are defined as being close to as understood by one of ordinary skill in the technique, and in one non-limiting embodiment the term is defined to be within 10%, in another embodiment within 5%, in another embodiment within 1% and in another embodiment within 0.5%. The term "coupled" as used herein is defined as connected, although not necessarily directly and not necessarily mechanically. A device or structure that is "configured" in a certain way is configured in at least that way, but may also be configured in ways that are not listed.

What is claimed is:

1. An ultrasonic bone analyzing device, comprising:
a transmission module including a transducer that transmits an ultrasonic signal inside a living body from an outer skin of the living body;
a reception module that receives with the transducer an echo signal that is a reflection wave of the transmitted ultrasonic signal from the inside of the living body; and
an analyzing module including a processor that generates analysis data indicative of a state of a cartilage using an amplitude value of an echo signal from the inside of the cartilage obtained from between a cartilage surface and a subchondral bone among the received echo signals,
wherein the transmission module is configured to transmit an ultrasonic signal at a predetermined frequency, the reception module is configured to receive the echo signal including two or more frequency components including the predetermined frequency and a second harmonic frequency of the predetermined frequency; and
wherein the analysis data is generated based on a value reflecting a relative ratio between an integral value of the amplitude value of the echo signals from inside the cartilage and an integral value of the amplitude value of the echo signals from the cartilage surface.

2. The ultrasonic bone analyzing device of claim 1, wherein the transmitted ultrasonic signal has two or more frequencies, and the analyzing module generates the analysis data based on an amplitude value of the echo signal from the inside of the cartilage for every frequency.

3. The ultrasonic bone analyzing device of claim 2, wherein the analyzing module further detects the echo signal from the cartilage surface contained in the received echo signal based on the amplitude value of the echo signal for every frequency.

4. The ultrasonic bone analyzing device of claim 2, wherein the analyzing module further detects the echo signal from the subchondral bone contained in the received echo signal based on the amplitude value of the echo signal for every frequency.

5. The ultrasonic bone analyzing device of claim 2, wherein the transmission module transmits the ultrasonic signals of different frequencies at different timings.

* * * * *